United States Patent
Silvers

(10) Patent No.: US 7,046,695 B2
(45) Date of Patent: *May 16, 2006

(54) SYSTEM AND METHOD OF DISHARMONIC FREQUENCY MULTIPLEXING

(75) Inventor: John Leroy Silvers, Miami, FL (US)

(73) Assignee: Bandwidth Technology Corp., New York, NY (US)

( * ) Notice: Subject to any disclaimer, the term of this patent is extended or adjusted under 35 U.S.C. 154(b) by 458 days.

This patent is subject to a terminal disclaimer.

(21) Appl. No.: 10/022,333

(22) Filed: Dec. 20, 2001

(65) Prior Publication Data

US 2002/0048287 A1   Apr. 25, 2002

Related U.S. Application Data

(63) Continuation of application No. 09/120,448, filed on Jul. 22, 1998, now Pat. No. 6,404,779.

(60) Provisional application No. 60/061,335, filed on Oct. 8, 1997.

(51) Int. Cl.
*H04J 1/02* (2006.01)

(52) U.S. Cl. .................................. 370/493; 370/537

(58) Field of Classification Search ............. 370/433, 370/437, 463, 436, 535, 536, 537, 538, 540, 370/542, 543, 544, 545, 468, 493, 494, 495; 375/240, 346, 347, 348

See application file for complete search history.

(56) References Cited

U.S. PATENT DOCUMENTS

| | | | | | |
|---|---|---|---|---|---|
| 5,844,900 | A | * | 12/1998 | Hong et al. | 370/342 |
| 5,875,179 | A | * | 2/1999 | Tikalsky | 370/315 |
| 6,320,911 | B1 | * | 11/2001 | Cucchi et al. | 375/259 |
| 6,341,247 | B1 | * | 1/2002 | Hreha et al. | 701/3 |
| 6,404,779 | B1 | * | 6/2002 | Silvers | 370/493 |
| 6,466,608 | B1 | * | 10/2002 | Hong et al. | 375/137 |

* cited by examiner

*Primary Examiner*—Kwang Bin Yao
(74) *Attorney, Agent, or Firm*—David D. Lowry; Brown Rudnick Berlack Israels LLP

(57) ABSTRACT

A multiplexing system and method for conveying simultaneously a multiplicity of communication channels over a single transmission medium. Multiplexing is effected by transforming a digital bit stream of each respective incoming channel into a corresponding prime frequency information stream and transmitting all of the prime frequency information streams over the single transmission medium. Digital bit streams carried on each incoming channel entering the system are in the form of binary "on" and "off" bits. These digital bits are converted into a corresponding information stream at a prime frequency component. Each prime frequency information stream is rendered distinctive and non-interfering with other prime frequency information streams during simultaneous transmission over the common medium due to the unique and heretofore unexploited mathematical properties of prime numbers. Expanded bandwidth is accomplished by grouping the prime frequency information streams into "chords" of disharmonic frequencies, and then transmitting the chord, composed of several discordant prime frequency information streams, over the single transmission medium.

20 Claims, 2 Drawing Sheets

SYSTEM AND METHOD OF DISHARMONIC FREQUENCY MULTIPLEXING

RELATED APPLICATION

This application is a Continuation of patent application Ser. No. 09/120,448, filed on Jul. 22, 1998, now U.S. Pat. No. 6,404,779 the disclosure of which is incorporated by reference herein. This application is related to Provisional Patent Application Ser. No. 60/061,335, filed on Oct. 8, 1997, the entire disclosure of which is incorporated herein by reference.

BACKGROUND OF INVENTION

1. Field of Invention

This invention relates generally to communications techniques, and more particularly to systems and methods for facilitating simultaneous transmission of a multiplicity of channels of information over a common transmission medium.

2. Status of Prior Art

Communication: The first copper-wire communication system was only capable of carrying one message per wire. Communications companies soon realized that, in order to enlarge their capacity to carry messages, they would have to devise ways to transmit several messages simultaneously over a single wire, for the cost of installing additional lines to accommodate increased demand was high. Companies that could reduce costs by putting more and more information over a single line, would have a competitive advantage. Discoveries in transmission techniques enabled more than one message to be transmitted per line, thereby paving the way for our telegraph and telephone industry to become viable commercial enterprises. The challenge of maximizing bandwidth and increasing line capacity was present from the very beginning of telecommunications technology, and is still with us today.

Presently, telecommunication networks provide the primary means for conveying voice and data traffic between source and destination. But existing telecommunication networks cannot handle the ever-increasing demand for transmission capacity. Rising population, lower telephone rates and increased data traffic over the Internet, all underscore the need to increase network capacity. As more and more bandwidth becomes available, higher bandwidth applications are quickly developed, such as higher resolution web pages and video-on-demand, which once again heightens the demand for increased bandwidth.

One way to satisfy an increasing demand for bandwidth is by installing additional transmission lines or by placing additional satellites in the sky. Both solutions are expensive and dictate substantial investments. Yet, even satellite solutions have limitations, for there is only a limited number of satellites that can be placed in geostationary orbit in the Clarke belt. After all, the Clarke belt is the only location where satellites, when viewed from the Earth's surface, remain substantially stationary, thereby permitting the use of fix-mounted dish antennas. Wireless systems, where the available radio spectrum is limited, also rely on bandwidth utilization or compression methods to expand the capacity of the system. To remain competitive, network service providers must endeavor to preserve the functionality of their existing networks, yet still be able to accommodate the increasing bandwidth demand to handle voice, data, and video transmission.

In conventional analog transmission, voice energy acts to compress the carbon granules in a microphone, thereby varying the microphones resistance to electrical current. Then the varying current, which varies in a manner analogous to the acoustical vibrations of the speaker's voice, is used to energize an electromagnet, actuating a diaphragm which vibrates to reproduce the original voice. Digital transmission adds several steps to this transformation, for the voice is converted to an electrical current pattern whose varying amplitude is measured thousands of times per second. These measurements are encoded as binary numbers, consisting of "0" and "1"s.

Unlike analog transmission which conveys the sound as a continuous wave form, in digital transmission, binary numbers are transmitted in representational encoding schemes. Binary digits or bits, may be transmitted singly, as discrete, on-off or zero/non-zero current pulses, or in groups as simultaneous pulses at different frequencies. At the receiving end, the bit stream is interpreted and the numbers reconstituted to modulate a current which drives a speaker. This method is "digital" because it entails conversion of an analog signal to numbers, and the transmission of digits in symbolic form.

Compression: There are several known methods which make possible the transmission of information with diminished bandwidth requirements. The most widely employed method relating to "compression" uses mathematical algorithms and dictionary tables to manipulate and "point" digital signals in such a way that each transmission channel uses less bandwidth to carry recognizable information. Compression is achieved by building a predictive model of the waveform, removing unnecessary elements, and reconstructing the waveform from the remaining elements.

When converting an analog signal into digital form, accurate conversion requires at least twice as many measurements (samples per second), as the highest frequency in the signal. The human voice generates sound frequencies in a range of 20 to 4,000 Hz. Hence, an ideal digital voice circuit, accepting an input in the range of 0–4,000 Hz, must sample this signal 8,000 times per second. Each sample is represented by 8 bits of data, and a single voice circuit, referred to as DS0, "digital signal level zero", carries 64,000 (8,000×8) bits of data.

Compression methods are based on reducing the number of bits required to convey a human voice or other data transmission. Currently utilized compression algorithms can produce acceptable voice quality using less than 64 kbs by eliminating frequencies not necessary for voice intelligibility, particularly those below 300 Hz and those above 3,300 Hz, and emphasizing the frequencies in the 1,000 Hz range that carry most of the voice energy. Methods that drop an excessive amount of input signal tend to frustrate high-speed tonal data transmission schemes employed by modems and faxes. Currently-employed compression algorithms and equipment are able to transmit acceptable voice quality with a compression ratio of 8:1, using 8,000 bps per channel.

With these compression methods, one channel can be made to carry eight voice conversations or eight fax transmission over a line that originally was able to carry only one voice conversation. Higher compression methods which transmit voice and data over a circuit using less than 8,000 bps, suffer from increasing degradation of voice quality and "loss," whereby at the receiving end of the line the voice in its original form is not clearly heard. Although new methods and algorithms may be employed to allow for clear voice transmission using less than 8,000 bps, there are appreciable limitations to these methods. All compression methods using algorithms suffer from greater and greater "loss" as compression ratios increase. Fax and video transmission that are more sensitive to bandwidth degradations are more limited in their acceptable compression ratios.

While the main advantage of digital compression is that it increases network efficiency, it can in some situations reduce it. Users of compression technology must ensure that their chosen compression method has the ability to transmit compressed data at the full capacity of the transmission lines. If not, consideration must be given to downgrading the speed of the transmission lines and sacrificing some of the throughput. Furthermore, the amount of time the computer spends compressing and decompressing the data can reduce efficiency.

Multiplexing: The most common form of telecommunications service is T-1 protocol. T-1 uses a form of multiplexing in which 24 voice or data channels, each with 8,000 bps, can simultaneously exist on one pair of twisted copper wires. The total bandwidth capacity of T-1 is 1.544 Mbps. Compression methods are used in conjunction with T-1 and other transmission protocols to maximize bandwidth. Common compression systems using a ratio of 8:1, can carry 192 simultaneous voice or data channels (24×8) over a T-1 line.

Network service providers employ methods for increasing bandwidth through the utilization of compression and multiplexing, the most common multiplexing scheme in the United States being the T-1 protocol. Conversations or digital information carried on each T-1 line or channel is rendered unique, and transmitted with other channels over a common medium by multiplexing.

An early method used by phone companies to render channels unique, is Frequency Division Multiplexing (FDM). In FDM, each of the 24 channels are rendered distinct by having each channel assigned to a frequency band. (For example, line 1 would use the frequency band of 0Hz–4,000 Hz, line 2 would use the 4,000 Hz–8,000 Hz band, etc.) But this method is best suited for analog signals which are subject to degradation and noise interference, and is therefore not commonly used at present. More common techniques are Time Division Multiplexing (TDM) and Statistical Multiplexing (STDM), often called "Packet switching." In TDM, each of the 24 channels (or lines) are rendered distinct by having each channel assigned to a particular, non-overlapping time slot. Frames of 24 time slots are transmitted, in which Channel 1 gets the first time slot in the frame, Channel 2 gets the second time slot and so on. STDM works in a similar manner to TDM, assigning channels on the basis of time division. But STDM takes advantage of statistical fluctuations, and instead of automatically assigning each channel to a time slot, STDM assigns only active channels to time slots. Hence, instead of transmitting channels in sequential order (1, 2, 3, 4, 5, 6) as in TDM, STDM only assigns time slots to channels that are being used, e.g., 1, 3, 1, 5, 1, 6 etc. This method creates higher bandwidth utilization than TDM.

OBJECTS AND SUMMARY OF THE INVENTION

In view of the foregoing deficiencies, a primary object of the invention is to provide multiplexing systems and methods for increasing the available bandwidth of transmission media including wire and wireless transmission, as well as satellite and fiber optic communication networks.

More particularly, an object of this invention is to provide systems and methods in which multiplexing of a multiplicity of incoming digital signals over a common transmission line is effected by Prime Frequency Multiplexing (PFM), wherein each channel transmitted over the common line is rendered distinct so as to avoid interference with any other channel.

A significant feature of PFM systems and methods operating in accordance with the invention is that information from each incoming channel is rendered distinctive from that of other incoming channels by assigning a unique respective prime number frequency to each of a plurality of corresponding incoming channels. Since no prime number is divisible by any other number, and the prime numbers assigned to the respective channels are not harmonically related, interference or cross talk is avoided even though a multiplicity of prime frequency components are simultaneously conveyed over the common line.

Briefly stated, these and other objects of the invention are attained in the form of multiplexing systems and methods for simultaneously conveying information corresponding to a multiplicity of incoming digital communication channels over a single transmission medium. Multiplexing is effected by transforming the respective incoming digital bit stream of each incoming channel into a corresponding prime frequency information stream, wherein different prime frequencies are used for different incoming channels. The prime frequency information streams are transmitted over the single transmission medium as discordant prime frequency chords. Digital bitstreams carried on each respective incoming channel entering the system in the form of binary "on"-"off" signals, are used to enable, disable, and/or control transmission of a corresponding information stream at a prime frequency. Each prime frequency information stream is rendered distinctive and non-interfering with other streams during simultaneous transmission over a common medium due to the unique and heretofore unexploited mathematical properties of prime number frequencies. Expanded bandwidth is accomplished by grouping the prime number frequency information streams into "chords" of disharmonic frequencies, and then transmitting these chords, containing a plurality of discordant prime number information streams, over the single transmission medium.

At the receiving end, a frequency-selective filtering mechanism separates information carried by a first prime number frequency information stream from information carried by other prime number frequency information streams. The first prime number frequency information stream corresponds to information which was originally present on a first incoming digital communications channel. This enables each individual prime number frequency information stream to be separated from the "chord" and once again restored to a digital stream of information corresponding to the original incoming digital communications channel.

The advantage of prime frequency multiplexing (PFM) is that it is not limited by time nor does it depend on a specific transmission medium. PFM can generate a greater number of distinct channels over electronically-based transmission media than multiplexing and compression systems heretofore known. Using PFM and the extra bandwidth it makes available, higher bit sampling can be effected and therefore greater fidelity in transmission. The common practice of telephone companies is to use a digital coding processor that take 8,000 samples per second at 8 bits, for a total of 64,000 bps. This number of bits per second is adequate for reproduction of a human voice. PFM can be programmed to code for the limits of the human ear which exceeds 12,000 Hz, rather than the human voice. Digitizing can be accomplished by taking 22,000+ samples, at 16 bits, for a total of 356,000+ bits per second. This can yield music of CD ROM quality over an existing telephone or data line.

BRIEF DESCRIPTION OF DRAWINGS

For a better understanding of the invention, as well as other objects and features thereof, reference is made to the accompanying drawings wherein.

DESCRIPTION OF INVENTION

A multiplexing system and method in accordance with the invention acts to expand the bandwidth capacity of existing digital transmission or storage media by simultaneously transmitting a plurality of information streams, each of which is assigned a unique prime number frequency, whereby the combination of information streams creates a plurality of disharmonic chords as a function of time.

In an embodiment of the invention relating to the increased capacity to transmit digital information over a standard transmission medium, the incoming information from each channel entering the system as a bitstream of binary coded information ("0"s and "1"s), is transformed to an equivalent coding in which "0"="no-play" and "1"="play", to be applied to generation and/or transmission and/or enablement of a signal generator operating at a prime number frequency. A prime number is a positive integer having no divisor except itself and the integer 1. Thus the number 31 is a prime number, whereas the number 30 is not.

Methods and systems in accordance with the invention may be used in conjunction with any transmission medium capable of carrying or transmitting a stream of information. Such transmission media includes copper wire, satellite transmission, wireless communications, radio frequency transmission over the air, radio frequency transmission through a coaxial cable, fiber optics, etc. and such protocols as T-1, ATM, Frame Relay, etc. Systems and methods developed in accordance with the invention will work with any digital information capable of being transmitted or stored, such as data, image, video or voice applications.

Figure 1:
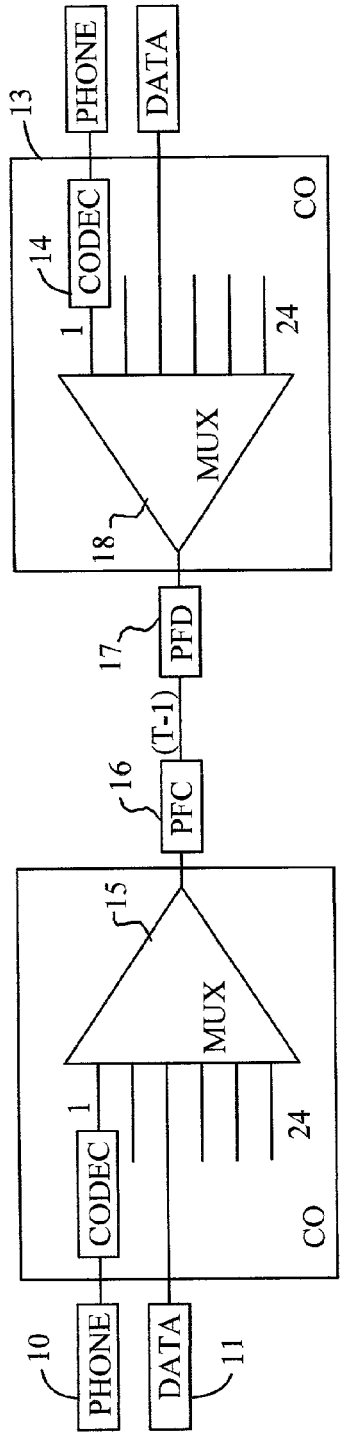
FIG. 1 is a block diagram of a telecommunications network constructed in accordance with the invention.

FIG. 1 is a block diagram of a portion of a telecommunications network in which the systems and methods of the present invention may be practiced. A portion of this network (phone 10, CO and 13 and CODEC 14) represent typical transmission components now employed by most telecommunications companies. PHONE 10 represents a standard analog telephone (sometimes referred to as a POTS phone—a "plain old telephone set") in a user's location. DATA 11 represents a computing device and/or a communications device equipped to transmit information in electronic form. CO 13 represents a telephone company Central Office, which is the physical location for local phone company hardware, including main switching equipment that connects all users in a local area to the PSTN (public switched telephone network).

CO 13 contains a plurality of digital switches by which phone calls are connected and routed across the PSTN. However, before incoming analog signals on a customer phone line can be digitally switched, these signals first need to be converted into a digital format. Accordingly, the CO is equipped with a CODEC 14 (coder-decoder). CODECs are coupled between one or more incoming telephone lines and one or more digital switches. More specifically, CODEC 14 represents a unit that converts an incoming analog signal (in the form of a sound wave) to a digital signal (in the form of binary on/off, or 0/1 signals).

Information coming into CODEC 14 from a DATA line is already in a digital format, and does not require an analog to digital conversion. The digital signal of each incoming line is connected to a 24-line MUX 15 (multiplexer). A 24-line MUX is a standard piece of telecommunications equipment that converges 24 incoming digital lines into one outgoing line, while maintaining each of the 24 lines as distinct voice or data channels. The line labeled "T-1" represents a T-1 transmission protocol, this being the most commonly employed protocol in telephony.

PFC 16 (Prime Frequency Coder) is a digital signal converter that converts each of a plurality of incoming binary digital streams to respective information streams, each information stream including a corresponding prime frequency component. PFC 16 transmits a plurality of information streams, each having its own corresponding prime frequency component, over a common transmission medium to a PFD 17 (Prime Frequency Decoder). Although the common transmission medium of FIG. 1 is shown as a T-1 line, this is for purposes of illustration only. The common transmission medium could be implemented using any form of wireless or wired communication, and/or by using various combinations thereof.

PFD 17 receives a plurality of incoming information streams, each stream having a unique prime frequency component. The incoming information streams are separated by using frequency-selective bandpass filters each designed to substantially pass a selected prime frequency component, while substantially rejecting other prime frequency components. PFD 17 then converts each of a plurality of separated and filtered streams back to corresponding digital signals (of "0"s and "1"s). These digital signals are then transmitted through another 24-line MUX 18 and CODEC 14 back to the user's phone 10.

Figure 2:
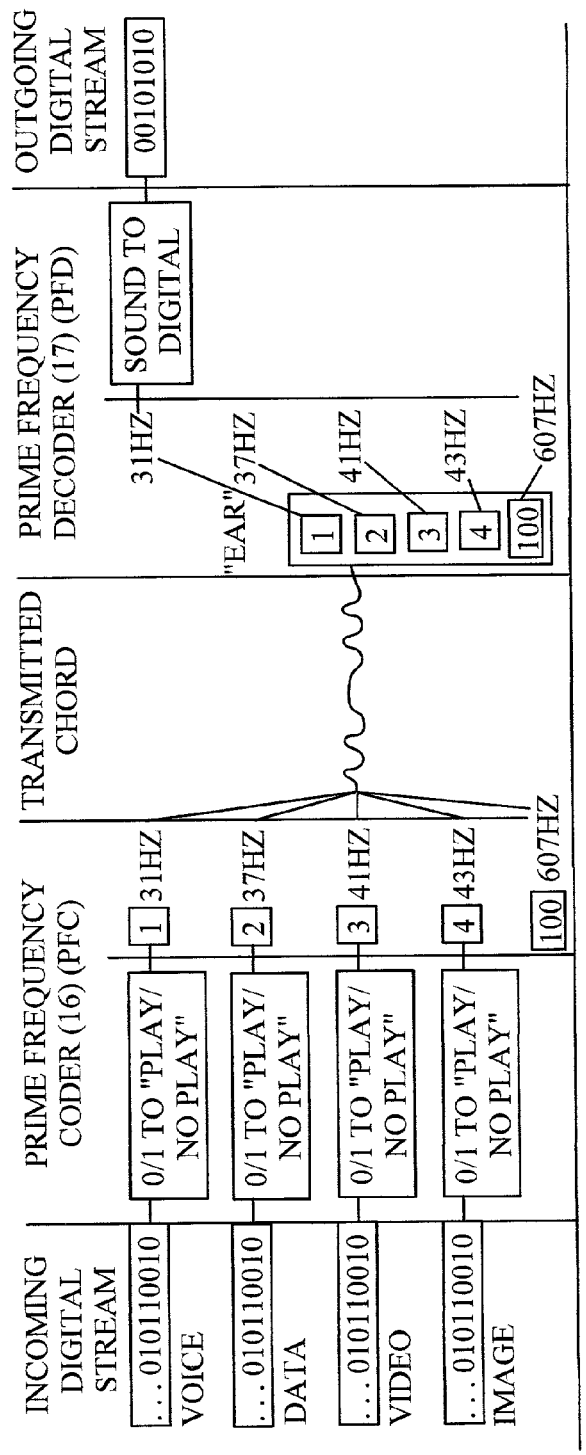
FIG. 2 is an enlarged block diagram of a portion of FIG. 1.

FIG. 2 is an enlarged block diagram of a portion of FIG. 1, illustrating the process and transformation that takes place within and between the PFC 16 and PFD 17. More specifically, FIG. 2 illustrates the manner in which several incoming digital streams (voice, data, video, and image) are transformed into corresponding information streams, each having a unique prime frequency component, combined into a disharmonic chord, transmitted over a common transmission medium, and then transformed back into digital voice, data, video, and image digital streams. In this manner, a plurality of information streams are transmitted between the PFC 16 and PFD 17 in such a way that the transferred information contained in each stream remains distinctive and non-interfering.

The portion of FIG. 2 labeled "INCOMING DIGITAL STREAM" is a representation of an incoming digital or binary bit stream in the form of "on/off" or "0/1" combinations, carried over the lines entering PFC 16. The incoming digital stream can carry any type of information capable of being translated into a digital format, including voice, music, data video frames, images, etc.

The section labeled "Prime Frequency Coder" (PFC-16) represents the system and its programming that transforms each of a plurality of digital streams of information ("0"s and "1"s) into a corresponding information stream represented by a corresponding prime frequency component. This process is accomplished by using computer software, a programmed computer chip, or software integrated within the hardware processing cards of a computer, router, or telecommunications switch, to control generation, enablement, and/or switching of prime frequency components.

Figure 3:
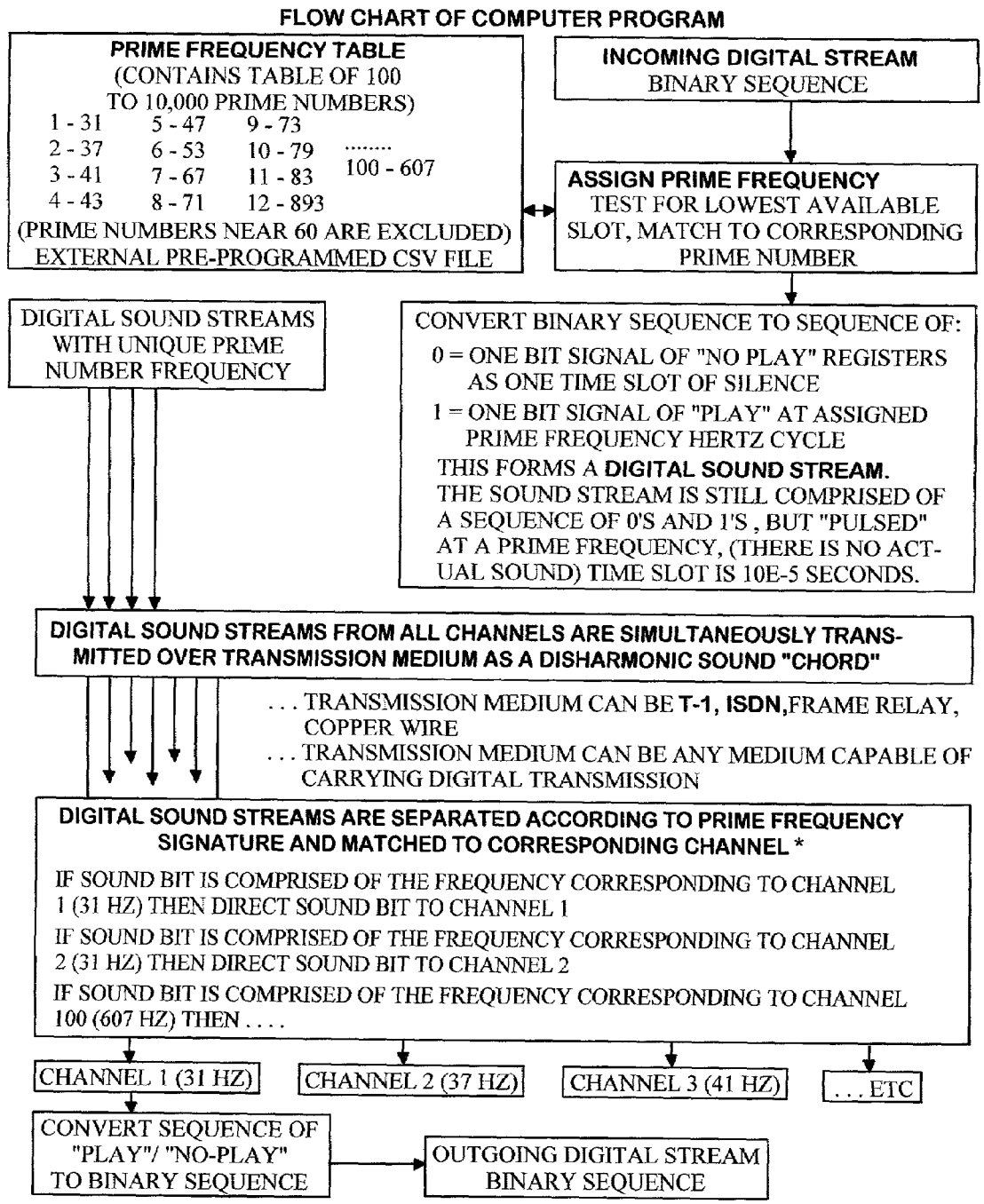
FIG. 3 is a flowchart setting forth an illustrative operational sequence to be performed by the systems of FIGS. 1 and 2

The flowchart for an illustrative computer program is shown in FIG. 3. The computer program may be contained within, and/or executed by, the PFC 16, which carries out the following operations:

(a.) It reads the digital stream (in the form of "0"s and "1"s) from each incoming voice or data line, (b.) It changes each bit of information in a respective incoming digital stream into a stream of corresponding bits of "play" and "no-play" signals to be applied to generation, enablement, and/or switching of a corresponding prime frequency component. Each time the program receives a "0" from the incoming digital stream, it converts that signal to a silent or "no-play" bit signal. And each time the program receives a "1" from the incoming digital stream, it converts the "1" to a digitally-represented sound or "play" bit signal, (c.) It assigns each stream of "play/no-play" commands to a corresponding unique prime number frequency as determined, for example, with reference to a table of prime number frequencies, and/or with reference to a representation of a prime number frequency stored in a computer-readable memory device.

With respect to the Prime Frequency Coder section of FIG. 2, the first incoming digital stream of information is assigned to location or slot 1 in a table of prime number frequencies. With each no-play/play signal, the program generates a sound "bit" containing "silence" and a "bit" played out at the Hertz frequency of 31 cycles per second.

In the same embodiment, the second digital stream of information is assigned to location or slot 2 in the table of prime number frequencies, and with each no-play/play signal, the program generates a sound "bit" containing "silence" and a "bit" containing the Hertz frequency of 37 cycles per second. In slot 3, the Hertz frequency is 41 Hz and is slot 4 it is 43 Hz.

(d.) It takes all the no-play/play bits from each incoming digitally-represented sound streams, and "plays out" each stream on its unique prime number frequency.

(e.) It combines a plurality of information streams at a plurality of different prime frequencies on a common transmission line and simultaneously transmits all of the prime frequency information streams over the transmission medium in the form of a disharmonic "chord" of multiple prime frequencies, for the frequencies are not harmonically related.

The software contained within PFC 16 and/or PFD 17 can be programmed to accommodate 10,000 or more incoming and outgoing lines, and it can be programmed to simultaneously transmit 10,000 or more channels of information.

In step (d.) above, the PFC programming and architecture functions roughly as a telecommunications multiplexer (MUX), whereby it accepts a plurality of incoming digital streams, assigns each stream to a unique channel (prime number frequency), and then simultaneously routes them all over a common transmission medium. Multiplexing devices often separate or divide channels of information by allocating time or frequency ranges. In a system in accordance with the invention, channels are rendered unique by allocation of each channel to a Hertz (or KHz, MHZ, Ghz, etc) frequency corresponding to a prime number. Hence there is no time or frequency range separation.

The intermediate section of FIG. 2, labeled "TRANSMITTED CHORD," represents the combination of all information streams simultaneously transmitted over a common transmission medium in the form of a disharmonic "chord" of prime number frequencies. It is "disharmonic" because all transmitted components have respective prime number frequencies. Hence no transmitted frequency is able to cancel out or "harmonize" with any other frequency in the chord. In the transmitted chord, each digitally-represented sound stream is formed from digitized signals "play" or "no-play" on a particular prime Hz frequency.

The reason no prime number frequency can "harmonize" with any other prime number frequency is that to be a harmonic it must be a multiple of another frequency. Therefore even though 100 or 10,000 prime number information streams are transmitted simultaneously across a single transmission medium, no prime number information stream will cancel out any other prime number information stream or interfere therewith. All prime number information streams will be transmitted over the transmission medium intact, with no loss of information. Transmission can also be accomplished over any medium, or protocol, for these techniques may be used in conjunction with other techniques for transmitting digital information, such as T-1, frame relay, ATM, satellite, wireless, ISDN, fiber optic, regular copper wire, etc.

The section labeled "Prime Frequency Decoder" (PFD-17) represents a device and its programming that acts as a "digital ear," allowing each line to pick up or "hear" only the "play/no-play" information stream of the specific prime frequency corresponding to its position in the prime frequency table.

Illustratively, the foregoing process can be accomplished with the use of 4 standard computer processing chips, or DSPs (Digital Signal Processors), each capable of a minimum of 10MIPS. Once the particular prime frequency information stream is "heard" in accordance with its assigned line location, the PFD changes the information stream ("play/no-play" at a prime frequency component) back into the original sequence (of "0"s and "1"s) of the incoming digital computer stream. This process may be accomplished by a computer software application contained within the software of a computer, a switching or routing device; or programmed into a computer chip and integrated within the hardware processing cards of a computer, router, or telecommunications switch.

PFD 17 restores or reverses the transformation carried out in PFC 16. The computer program contained in PFD 17 effectively functions as an "ear" that allows each receiving line to hear only information corresponding to a given prime frequency component. This is the component which was previously assigned to an incoming digital stream which is now to be reconstructed. Moreover, information transmitted on each of a plurality of prime number frequencies is transformed back into binary form and rendered as a distinct channel which is linked to a single outgoing line.

The computer program implements the following functionalities in conjunction with the PFD 17 (FIG. 1): (a.) First of all, the PFD 17 acts as a "deMUXer," where one communications line carrying all the prime number frequencies of one or more disharmonic chords is received and then separated into a plurality of single lines, based upon the prime number frequency components of the received chords. If 100 prime number frequencies are simultaneously sent over the transmission medium, the PFD separates each prime number frequency information stream and routes each stream coming over a particular frequency, to its corresponding assignment represented by a particular one of the 100 outgoing lines, (b.) The PFD 17 transforms an incoming information stream at a particular prime number frequency, which was previously generated using a sequence of "play/no-play" signals, into a digital computer stream of corresponding signals of "0"s and "1"s. Each time the program detects the presence of a given prime number frequency component, corresponding to previous implementation of a "play" signal, on the incoming prime number frequency information stream, it converts that signal to a "1,"0 and each time the program detects the absence of a given prime number frequency component, corresponding to previous implementation of a "no-play" signal, on the incoming prime number frequency information stream, it converts that signal to a "0".

(c.) The PFD 17 routes the restored digital information to its corresponding channel.

In the embodiment shown in FIG. 2, a prime frequency component information stream is transmitted as a disharmonic chord. The chord includes prime frequency components of 31 Hz, 37 Hz, 41 Hz, 43 Hz, and 607 Hz. These values are provided for illustrative purposes only, as particular system applications may utilize specific prime frequency components within a specified range of values, and/or eliminate prime frequency components which are relatively close in frequency to other prime frequency components. In the example of FIG. 2, each prime frequency component is provided as a sinusoidal wave, but this is not an absolute requirement, as various other types of alternating and/or periodic waveforms could be utilized, so long as the periodicity and/or alternating occurs substantially at a prime frequency. The block labeled 'EAR', representing a portion of PFD 17, includes a plurality of bandpass filters, each filter equipped to respond substantially to a particular prime frequency component, and to substantially reject other prime frequencies. For example, a first bandpass filter (reference numeral 1) passes a prime frequency component of 31 Hz. A second bandpass filter (reference numeral 2) passes a prime frequency component of 37 Hz, a third bandpass filter (reference numeral 3) passes a prime frequency component of 41 Hz, a fourth bandpass filter (reference numeral 4) passes a prime frequency component of 43 Hz, and an Nth ($100^{th}$) bandpass filter (reference numeral 100) passes a prime frequency component of 607 Hz. The output of first bandpass filter 1, corresponding to the incoming digital stream labeled 'VOICE', can only hear 31 Hz frequency components (i.e., sounds) on the transmitted chord. The output of this filter can hear no other sounds (i.e., no other prime frequency components) transmitted on the chord. The output of second bandpass filter 2, corresponding to the incoming digital stream labeled 'DATA', can only hear sound transmitted at 37 Hz. The 'sound' stream provided at the output of the first bandpass filter 1 (transmitted at 31 Hz) is picked up by the PFD 17 sound-to-digital converter, changed to an outgoing digital stream (0/1), and routed as digital information over the first outgoing line.

The 'sound' stream at the output of the second bandpass filter 2 (transmitted at 37 Hz) is picked up by the PFD 17 sound-to-digital converter, changed to an outgoing digital stream (0/1), and routed as digital information over a second outgoing line, and so on with outputs from the remaining bandpass filters, which are used to reconstruct digital information on other outgoing digital lines.

The sound-to-digital converter of FIG. 2 converts electronic signals, in the form of sinusoidal, periodic, and/or alternating waveforms, into digital (binary) information. Accordingly, the term "sound" as used herein does not refer to acoustical vibrations, but instead to electronic signals in the form of sinusoidal, periodic, and/or alternating waveforms This invention can be used to increase bandwidth capacity on existing transmission media and/or in conjunction with satellite transmission protocols. This invention has the following advantages:

(a.) No other multiplexing or compression method uses prime number frequencies to render channels unique. Its multiplexing function can be applied to a single channel, and/or a channel that has already been separated into 24 channels by a multiplexer.

(b.) It can be used on a single T-1 channel, a fractional T-1, or a T-1.

(c.) It can be applied to any digital transmission protocol.

(d.) It can be applied to any medium capable of carrying electronically-coded digital information.

(e.) It can carry a large number of unique voice and data channels on a single line.

(f.) It does not render channels unique by using time division, for such division has severe limitations.

(g.) It does not rely on compression to increase bandwidth, and it is not subject to the limitation of using algorithms.

(h.) it provides an inexpensive means of increasing bandwidth.

While there has been shown a preferred embodiment of a system and method of disharmonic frequency multiplexing, it is to be understood that many changes may be made therein without departing from the spirit of the invention.

Thus the PFC multiplexing system and method can be applied not only to the communication of digital information, but also to its storage in which a plurality of digital information streams in the form of a disharmonic chord are stored in a CD ROM or other storage medium.

I claim:

1. A system for effectively increasing transmission bandwidth by transmitting a plurality of simultaneous information streams over a transmission medium, the system comprising: a. a digital receiving mechanism for receiving incoming streams of digital information on each of a plurality of incoming digital lines, the digital information being in a binary format of "0"s and "1"s, b. an assignment mechanism for generating respective streams of "no-play" and "play" commands using digital information on each of a plurality of corresponding incoming streams; c. a signal generation mechanism equipped to generate a plurality of prime number frequency components; d. a switching mechanism, coupled to the signal generation mechanism, for rendering the digital information on each of the plurality of incoming streams unique by applying "no-play" and "play" commands of a respective incoming stream to a corresponding prime number frequency component to be generated by the signal generation mechanism, to thereby generate a corresponding plurality of prime number frequency component information streams; and e. a transmission mechanism for simultaneously transmitting the plurality of prime number frequency component information streams over the transmission medium in the form of disharmonic chords, whereby respective prime number frequency component information streams represent corresponding incoming digital lines.

2. The system of claim 1 further comprising an information stream receiving mechanism for receiving an information stream in the form of disharmonic chords transmitted on the transmission medium; the information stream receiving mechanism including a plurality of frequency-selective filters, each of respective filters substantially passing a corresponding prime frequency component and substantially rejecting a plurality of other prime frequency components, such that the frequency-selective filters substantially isolate a prime frequency component included in the disharmonic chords, to thereby provide a plurality of isolated prime frequency components, each of respective isolated prime frequency components representing a corresponding incoming digital line.

3. The system of claim 2 further including a conversion mechanism, coupled to the information stream receiving mechanism, for converting each of a plurality of isolated prime frequency components back into a stream of digital information.

4. The system of claim 1 wherein at least two of: a. the digital receiving mechanism, b. the assignment mechanism, c. the signal generation mechanism; d. the switching mechanism, and e. the transmission mechanism are integrated into the software programming of a computing mechanism, telecommunications switching device, and/or computer server.

5. The system of claim 1 wherein: a. the digital receiving mechanism, b. the assignment mechanism, c. the signal generation mechanism; d. the switching mechanism, and e. the transmission mechanism are implemented by one or more application-specific integrated circuit chips (ASICs).

6. The system of claim 1, wherein at least two of: a. the digital receiving mechanism, b. the assignment mechanism, c. the signal generation mechanism; d. the switching mechanism, and e. the transmission mechanism, are implemented by an IP server that transmits voice over IP data lines, as used in Internet Telephony devices.

7. The system of claim 1, wherein the transmission medium utilizes any of T-1 protocols, frame relay protocols, satellite communication links, ATM (asynchronous transfer mode) protocols, and fiber optics communication links.

8. The system of claim 1 wherein at least two of: a. the digital receiving mechanism, b. the assignment mechanism, c. the signal generation mechanism; d. the switching mechanism, and e. the transmission mechanism, are implemented using one or more computer microprocessors.

9. The system of claim 1 wherein at least two of: a. the digital receiving mechanism, b. the assignment mechanism, c. the signal generation mechanism; d. the switching mechanism, and e. the transmission mechanism, are implemented using megabit computer processing chips or computer processing chips of a determinable bit size.

10. The system of claim 1 wherein at least two of: a. the digital receiving mechanism, b. the assignment mechanism, c. the signal generation mechanism; d. the switching mechanism, and e. the transmission mechanism, are implemented using a computer processing chip where the bit size is any arbitrarily determined number, including but not limited to 64 bits or 128 bits, such that the computer processing chip may be programmed with a number of instructions approaching the maximum instruction programming capacity of the processing chip.

11. The system of claim 10 wherein the transmission mechanism is controlled using processor instructions, and the computer processor chip is equipped with a processor of any size, including but not limited to a 100 bit processor, a 1,000 bit processor, and a 10,000 bit processor.

12. The system of claim 11, wherein computer and machine instructions are stored on a computer readable data storage medium using representations of prime number Hertz frequencies.

13. The system of claim 1, wherein the incoming streams of digital information represent any of video, images, data and voice.

14. A system for effectively increasing information storage capacity of a computer-readable data storage medium by storing a plurality of prime number frequency component information streams on the data storage medium, the system comprising: a. a digital receiving mechanism for receiving incoming streams of digital information on each of a plurality of incoming digital lines, the digital information being in a binary format of "0"s and "1"s, b. an assignment mechanism for generating respective streams of "no-play" and "play" commands using digital information on each of a plurality of corresponding incoming streams; c. a signal generation mechanism equipped to generate a plurality of prime number frequency components; d. a switching mechanism, coupled to the signal generation mechanism, for rendering the digital information on each of the plurality of incoming streams unique by applying "no-play" and "play" commands of a respective incoming stream to a corresponding prime number frequency component to be generated by the signal generation mechanism, to thereby generate a corresponding plurality of prime number frequency component information streams; and e. a data storage mechanism for storing the plurality of prime number frequency component information streams on the data storage medium in the form of electronic representations of disharmonic chords, whereby respective prime number frequency component information streams represent corresponding incoming digital lines.

15. The system of claim 14, wherein the computer-readable data storage medium comprises any of magnetic tape, optical data storage media, compact discs (CDs), CD-R and CD-RW discs, computer hard drives, floppy discs, bubble memory, semiconductor memory chips, and molecular memory chips.

16. The system of claim 15 further comprising an information stream reading mechanism for reading an information stream in the form of disharmonic chords stored on the data storage medium; the information stream reading mechanism including a plurality of frequency-selective filters, each of respective filters substantially passing a corresponding prime frequency component and substantially rejecting a plurality of other prime frequency components, such that the frequency-selective filters substantially isolate a prime frequency component included in the disharmonic chords, to thereby provide a plurality of isolated prime frequency components, each of respective isolated prime frequency components representing a corresponding incoming digital line.

17. The system of claim 16 further including a conversion mechanism, coupled to the information stream reading mechanism, for converting each of a plurality of isolated prime frequency components back into a stream of digital information.

18. The system of claim 14, wherein the incoming streams of digital information represent any of video, images, data and voice.

19. A method of conveying over a common transmission medium, without mutual interference, information from a plurality of incoming binary bit streams, the method comprising the steps of:
  a. receiving incoming streams of digital information on each of said plurality of incoming binary bit streams, the digital information being in a binary format of "0"s and "1"s, b. generating respective streams of "no-play" and "play" commands using digital information on each of a plurality of corresponding incoming binary bit streams;

c. generating a plurality of prime number frequency components;

d. rendering the digital information on each of the plurality of incoming binary bit streams unique by applying "no-play" and "play" commands of a respective incoming binary bit stream to a corresponding generated prime number frequency, to thereby generate a corresponding plurality of prime number frequency component information streams; and e. simultaneously transmitting the plurality of prime number frequency component information streams over the transmission medium in the form of disharmonic chords, whereby respective prime number frequency component information streams represent corresponding incoming binary bit streams.

20. A method as set forth in claim 19, further comprising the steps of receiving a disharmonic chord, separating the chord into individual prime frequency component streams, and decoding each individual prime frequency component stream to recover binary information carried thereby.

* * * * *